(12) United States Patent
Hribar et al.

(10) Patent No.: US 11,499,130 B2
(45) Date of Patent: Nov. 15, 2022

(54) METHODS AND DEVICES FOR CELL CULTURE

(71) Applicant: CYPRE, INC., San Francisco, CA (US)

(72) Inventors: Kolin C. Hribar, San Francisco, CA (US); Andrew Kelly, Boise, ID (US)

(73) Assignee: Cypre, Inc., San Francisco, CA (US)

(*) Notice: Subject to any disclaimer, the term of this patent is extended or adjusted under 35 U.S.C. 154(b) by 859 days.

(21) Appl. No.: 16/156,663

(22) Filed: Oct. 10, 2018

(65) Prior Publication Data

US 2019/0106667 A1 Apr. 11, 2019

Related U.S. Application Data

(60) Provisional application No. 62/570,538, filed on Oct. 10, 2017.

(51) Int. Cl.
*C12M 1/12* (2006.01)
*B01L 3/00* (2006.01)

(52) U.S. Cl.
CPC ............ *C12M 25/14* (2013.01); *B01L 3/50* (2013.01); *B01L 3/502* (2013.01); *B01L 3/5085* (2013.01); *B01L 3/50855* (2013.01)

(58) Field of Classification Search
CPC .......... C12M 25/14; B01L 3/50; B01L 3/502; B01L 3/5085; B01L 3/50855
See application file for complete search history.

(56) References Cited

U.S. PATENT DOCUMENTS

| 2009/0136583 | A1 | 5/2009 | Park |
| 2010/0112690 | A1* | 5/2010 | Eddington ............ C12M 29/10 435/297.5 |
| 2014/0141503 | A1 | 5/2014 | Hong et al. |
| 2016/0175800 | A1 | 6/2016 | Murphy et al. |
| 2017/0087766 | A1 | 3/2017 | Chung |

FOREIGN PATENT DOCUMENTS

WO 2010105845 9/2010

OTHER PUBLICATIONS

International Search Report for related PCT application with serial No. PCT/US2018/055219 filed on Oct. 10, 2018.

* cited by examiner

*Primary Examiner* — Robert J Eom
(74) *Attorney, Agent, or Firm* — Fish IP Law, LLP (57) ABSTRACT

Devices and methods are provided that allow for the casting of flat, controlled thickness layers of gel or polymer on a test surface, such as within the wells of a microplate. A spacer device is interposed between the test surface and the planar lower face of a movable pillar, defining a highly uniform volume. Addition of a gel or polymer precursor in solution followed by curing generates a highly uniform gel or polymer layer with a planar upper surface within this volume, which is exposed on removal of the pillar. In some embodiments a group of pillars is provided in a manifold that provides spacing and arrangement corresponding to a group of test wells. The pillars are mounted in the manifold so as to provide translation movement normal to the test surface, allowing them to rest against the spacer device and facilitating gentle removal from the wells. A variety of spacer devices are considered, including beads, flattened rings, and toroidal spacers.

10 Claims, 7 Drawing Sheets

METHODS AND DEVICES FOR CELL CULTURE

This application claims the benefit of U.S. Provisional Application No. 62/570,538 filed on Oct. 10, 2017. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is cell culture, particularly culture of cells attached to a biological matrix.

BACKGROUND

The following description includes information that may be useful in understanding the present invention. It is not an admission that any of the information provided herein is prior art or relevant to the presently claimed invention, or that any publication specifically or implicitly referenced is prior art.

The background description includes information that may be useful in understanding the present invention. It is not an admission that any of the information provided herein is prior art or relevant to the presently claimed invention, or that any publication specifically or implicitly referenced is prior art.

Cultured cells provide an invaluable tool for screening and evaluating pharmaceutical compounds, permitting large scale screening studies that are not feasible using live animals. While some of such studies can be performed on cells in a liquid suspension, increasingly studies are being performed on cells that are cultured while attached to a solid matrix. Use of such solid matrices permits studies involving cells that are not suitable for culture in suspension. In addition, attachment of molecules that mimic the cell's natural environment (for example, components of the extracellular matrix), growth factors, and/or similar biomolecules can support development of more physiologically relevant cellular morphology. In some instances cells cultured in such a manner can organize and/or differentiate to form rudimentary tissues or portions thereof.

Typically such a solid substrate is provided by a microwell plate. These plates are generally constructed (at least in part) from a transparent plastic, such as polystyrene, and include from 24 to 396 open-topped wells arranged in rows and columns. Such plates can be obtained with various surface treatments, such as a poly-lysine coating, that are useful in cell culture. If a more complex or unstable surface treatment (such as a biopolymer coating) is desired, however, the user typically instills the desired coating compound into individual wells as a solution prior to use. Unfortunately, a simple coating of biopolymer noncovalently bound to the interior plastic surface of a test well is not sufficient for many applications.

In order to provide for a more suitable environment for cell culture, gel-forming solutions have been used to form gel layers that include desirable biopolymers (such as collagen) within the wells of microwell plates. Unfortunately, simply instilling a volume of liquid into a well does not provide an optimal result. For some gel-forming materials the volume required for filling or partially filling the wells of a microwell plate can be prohibitively expensive. Also, the surface of the resulting gel is inevitably curved due to surface tension. This interferes with observation of the cells growing on the gel surface. In addition, great care must be taken to avoid the formation of air bubbles at the surface of the liquid. The Ibidi microwell plate provides a well that includes a small central depression, which helps to reduce the volume of gel-forming solution required. Unfortunately this approach does not address the problems of bubble formation and surface curvature.

One approach to addressing these issues is found in United States Patent Application Publication No. 2014/0141503 (to Hong et al.), which describes the use of a substrate that carries a set of pillars that project upwards from the substrate surface. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. A liquid coating material is dispensed over these pillars and fills the space between them, generating a liquid:air interface with multiple small menisci between the pillars. Such an approach, however, exchanges a single large meniscus for a dimpled surface, and fails to completely eliminate the meniscus effect. In addition, the fabrication of such pillars within the wells of a microplate would be expected to be technically challenging.

U.S. Patent Application Publication No. 2016/0175800, to Murphy and Le, describes the application of a set of "negative inserts" into wells of a microwell plate that contain a hydrogel precursor solution. These negative inserts provide a central channel within each well; removal of the set of negative inserts following gel formation leaves a central pillar of hydrogel within each well. In order to permit flow of hydrogel precursor solution into this central channel, however, requires that these negative inserts be open to the atmosphere in order to equalize pressure. As such the liquid hydrogel precursor within these negative insert would have a meniscus that would necessarily be reflected in the upper surface of the resulting hydrogel pillar.

Thus, there is still a need for methods and devices that provide suitable surfaces for cell culture.

SUMMARY OF THE INVENTION

The inventive subject matter provides apparatus, systems and methods that provide a highly uniform layer of gel or polymer on a test surface, such as a well of a microplate. Such gel or polymer layers minimize consumption of gel or polymer precursors and are highly suitable for optical characterization or image capture of cells cultured on and/or in the gel or polymer layer.

One embodiment of the inventive concept is a device for generating a patterned hydrogel that includes a well having a lateral wall and a floor, a pillar dimensioned to lie inside the well and having a planar lower face, and a spacer configured to provide a separation distance (e.g. from 10 μm to 5 mm) between the floor of the well and the lower face of the inserted pillar. In some embodiments two or more pillars are provided on a pillar support in a slidable fashion, and are positioned to correspond to a corresponding set of wells. The spacer can be coupled to the floor of the well or to the lower face of the pillar. In some embodiments the spacer has multiple components, some of which are coupled to the floor of the well and some of which are coupled to the lower face of the pillar. Suitable spacers include one or more beads, a ring, a partial ring, and/or one or more polygons, where at least one linear dimension of the spacer corresponds to the separation distance between the floor of the well and lower face of the pillar. Pillars can be constructed using hydrophobic and/or low friction materials to minimize mechanical stress on the gel or polymer upon removal. The test surface (e.g. the floor of a test well) can include a biocompatible polymer or glass, and in some embodiments is at least partially transmissive of optical and/or ultraviolet wavelengths.

Another embodiment of the inventive concept is a method for generating a patterned hydrogel by obtaining a patterning device that includes a well with a lateral wall and a floor, a pillar dimensioned to lie within the volume of the well and having a planar lower face, and a spacer configured to provide a separation distance (e.g. from 10 μm to 5 mm) between the floor of the well and the lower face of the pillar. In some embodiments two or more pillars are provided on a pillar support in a slidable fashion, and are positioned to correspond to a corresponding set of wells. A volume of a hydrogel precursor is added to the well, and the pillar is inserted into the well so such that the spacer is interposed and in contact with the floor of the well and the lower face of the pillar. This defines a hydrogel volume. After allowing enough time to pass for the hydrogel precursor to cure a hydrogel layer is formed within the well. In some embodiments the pillar is removed after the curing time has passed, thereby exposing a gel or polymer surface. This exposed gel or polymer can be subjected to additional processing steps. The spacer can be coupled to the floor of the well or to the lower face of the pillar. In some embodiments the spacer has multiple components, some of which are coupled to the floor of the well and some of which are coupled to the lower face of the pillar. Suitable spacers include one or more beads, a ring, a partial ring, and/or one or more polygons, where at least one linear dimension of the spacer corresponds to the separation distance between the floor of the well and lower face of the pillar. Pillars can be constructed using hydrophobic and/or low friction materials to minimize mechanical stress on the gel or polymer upon removal. The test surface (e.g. the floor of a test well) can include a biocompatible polymer or glass, and in some embodiments is at least partially transmissive of optical and/or ultraviolet wavelengths.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1.

FIG. 2.

FIG. 3.

FIG. 4.

FIG. 5.

FIG. 6.

FIG. 7.

FIGS. 8A and 8B.

FIG. 9.

FIG. 10.

DETAILED DESCRIPTION

The following description includes information that may be useful in understanding the present invention. It is not an admission that any of the information provided herein is prior art or relevant to the presently claimed invention, or that any publication specifically or implicitly referenced is prior art.

Devices and methods of the inventive concept facilitate the generation of gel or polymer layers within the wells of a microplate or on any suitable test surface, where the gel or polymer layers are flat (e.g. lacking a meniscus) and have a highly uniform thickness (e.g. varying less than ±10%). This is achieved by providing a spacing device on the floor of the well and applying a sliding pillar to the well. Contact between the lower face of the sliding pillar with the spacing device defines a space or volume within which the flat and highly uniform layer of gel or polymer can form. A variety of spacing devices, including beads and circular devices, are suitable. Sliding pillars can be provided mounted in a manifold that provides controlled spacing and can support a mechanism for manipulating the sliding pillars (e.g. application of reduced pressure or a magnetic field). It should be appreciated that the highly uniform gel or polymer layers thus produced, in addition to minimizing the consumption of costly gels and/or polymers, can be utilized in studies of living cells and are highly suitable for imaging and optical characterization.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The inventive subject matter provides devices and methods in which a well for cell culture on a gel, polymer, or similar surface is provided. The well is provided with a pillar that is dimensioned to fit within the well and that has a flat lower face, and is also provided with one or more spacers that is(are) positioned between the floor of the well and the flat lower face of the pillar when the pillar is inserted in the well. On instilling a gel-forming solution into a well and placing the pillar in the well the flat lower face of the pillar, the bottom of the well, and at least a portion of the side(s) of the well form a defined volume within which gel formation occurs. Insertion of the pillar can displace some or all of any bubbles formed on addition of the gel-forming solution, and on removal of the pillar the gel bed formed within the well has a flat upper surface (reflecting the flat geometry of the lower face of the pillar). For multi-well plates pillars can be provided in a holder or manifold that maintains the pillars in an arrangement and spacing that reflects that of the wells of the plate. In some embodiments the pillars are supported in the holder in a fashion that permits the pillars to slide within the holder while maintaining their arrangement and spacing.

A wide variety of spacers can be used. In some embodiments one or more beads (i.e. discrete particulate bodies) act as spacers by being interposed between the floor of a well and the lower face of a pillar. In some embodiments the spacer is a flattened ring or a toroid that lies around the periphery of the well bottom in the assembled device. In other embodiments the spacer is a partial flattened ring (i.e. having a generally circular arrangement that includes a gap) that is similarly arranged. In still other embodiments the spacer can be a circular or approximately circular torus or partial torus (i.e. having a generally circular arrangement that includes a gap) of fiber, wire, extruded polymer, or similar material that is arranged to lie at least partially around the periphery of the well bottom of the assembled device. Alternatively, more than one spacing device can be used. For example, a number of beads or spheres having a diameter that corresponds to the desired depth of the gel bed (or height of a volume defined by the well and an inserted pillar) can be used as spacers. Similarly, one or more triangular, quadrilateral, pentagonal, hexagonal, or polygonal features having a linear dimension corresponding to the desired depth of the gel bed (or height of a volume defined by the well and an inserted pillar) can act as a spacer.

In some embodiments a spacer can be coupled to or placed against a test surface (such as the floor of a test well) prior to insertion of a pillar. In other embodiments the spacer can be coupled to the lower face of the pillar. In still other embodiments the spacer can have multiple components, a portion of which are coupled to the lower face of the pillar and a portion of which are coupled to or placed against the test surface. When particulate or bead spacer are used, the size and density of the particles or beads can be selected such that they can be suspended in a gel or polymer precursor that is instilled onto a test surface or into a test well prior to or at the time of pillar insertion. In such an embodiment the portion of particulates or beads that are interposed between the test surface and the lower face of the pillar can act as the spacer.

Figure 1:
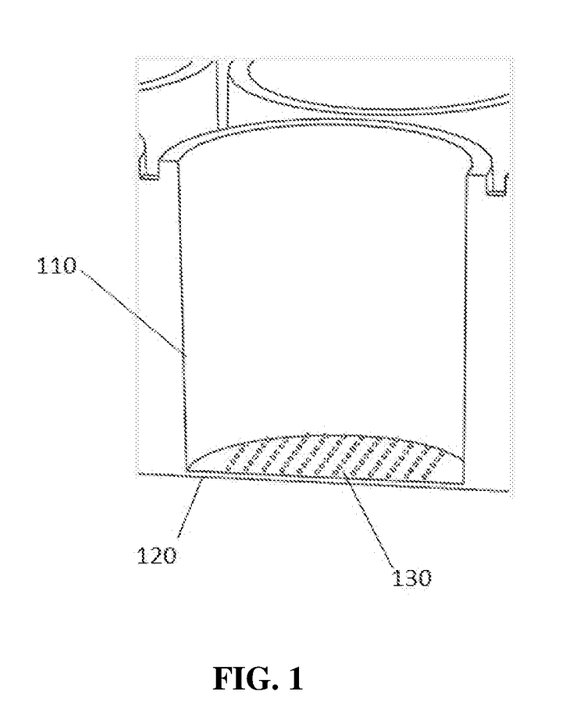
FIG. 1 depicts an embodiment of the inventive concept in which beads are utilized as spacers. A cross section of a well with bead spacers placed on the floor of the well is shown.
Figure 2:
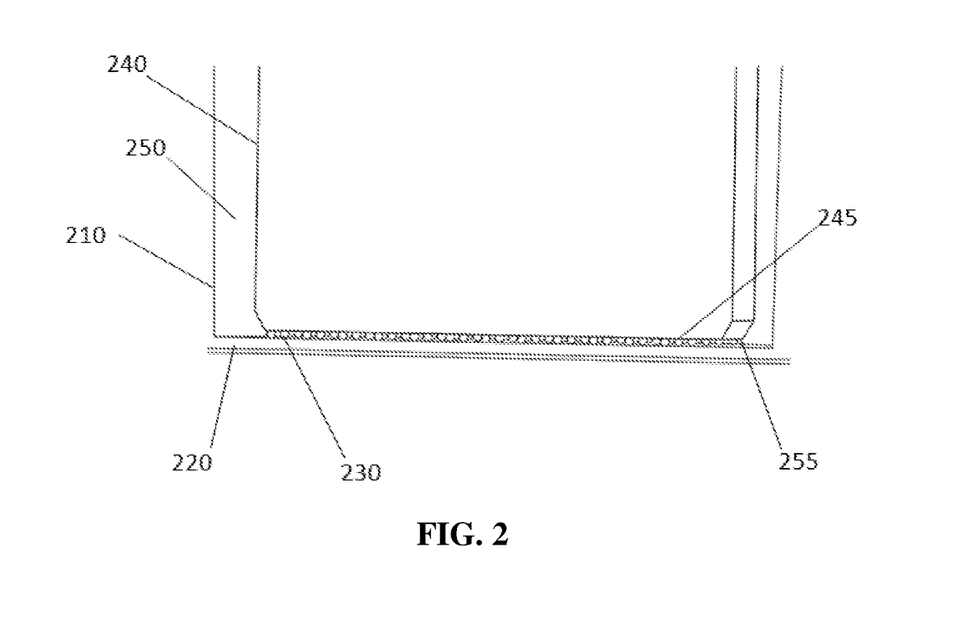
FIG. 2 depicts an embodiment of the inventive concept in which beads are utilized as spacers. A cross section of a well with bead spacers and an inserted pillar is shown.

FIGS. 1 and 2 show examples of beads as spacers of the inventive concept. FIG. 1 depicts a well of a multiwell plate, having a side 110 and a floor 120. An array of beads 130 is arranged on the floor of well to act as a spacer. While depicted as an ordered array, in some embodiment the beads can be arranged randomly. Such a random arrangement of beads can be provided by, for example, dispensing a volume of beads in suspension into the well, selecting a bead concentration that provides a dispersed monolayer of beads (i.e. one in which the mean distance between beads is at least 1 mean bead diameter) when the beads have settled to the floor of the well. While a plurality of beads are depicted, in some embodiments a single bead can be used.

Although depicted as spherical beads can be of any suitable shape, including oblate spheroids, cylinders, cubes, etc. Similarly, beads can be of any suitable composition capable of providing sufficient mechanical support for a pillar. Suitable materials include synthetic polymers (e.g. polyethylene, polypropylene, polystyrene, polyamide, silicon, etc.), biopolymers (e.g. crosslinked gelatin, crosslinked polysaccharides, etc.), metals (e.g. stainless steel, titanium, etc.), and/or minerals. Beads can be encoded (e.g. by color) to indicate the type of bead selected and provide information regarding the contents and/or gel depth in a particular well. In some embodiments beads can include growth factors and/or other components that can influence cell growth proximate to the bead.

FIG. 2 shows an example of a well of a multiwell plate that utilizes an arrangement of beads as a spacer, into which a pillar has been inserted. As shown, the well has a side 210 and a floor 220 on which a plurality of beads 230 are deposited as a dispersed monolayer. A pillar 240 is inserted into the well, and has a lower face 245 that rests on top of the beads. The pillar is sized and positioned within the well to provide a lateral gap 250 between the side of the well and the lateral wall of the pillar. A controlled height gap 255 is generated between the lower face of the pillar and the floor of the well by virtue of the pillar resting on the bead spacer. Addition of a polymerizable or gel-forming liquid to a well so arranged (or the presence of such a polymerizable or gel-forming liquid prior to or at insertion of the pillar into the well) can result in the formation of a controlled thickness gel layer within the controlled height gap, which remains in place upon removal of the pillar from the well.

Although depicted in FIG. 1 as being placed on the floor of a well, in some embodiments beads can be placed on the lower face of a pillar, or on both the lower face of the pillar and the floor of the well. Alternatively, beads can be provided in suspension with a liquid pre-gel mixture that is added to the well and locate to between the well floor and the pillar on insertion of the pillar. Beads can be arrayed, as shown, or randomly distributed.

Figure 3:
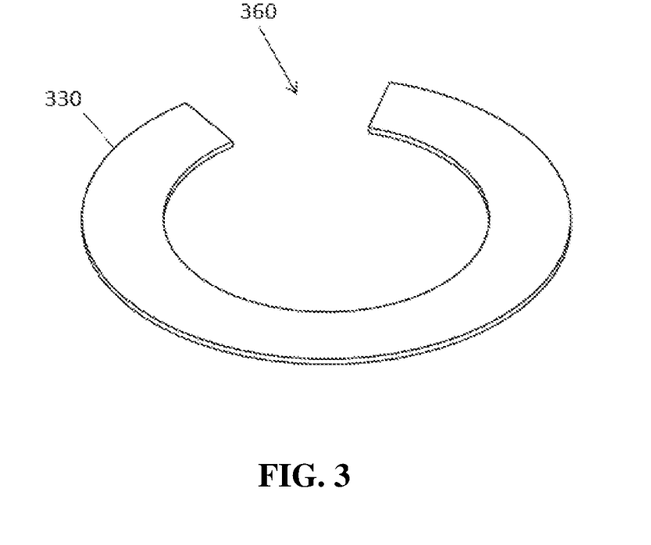
FIG. 3 depicts partial flattened ring spacer of the inventive concept.
Figure 4:
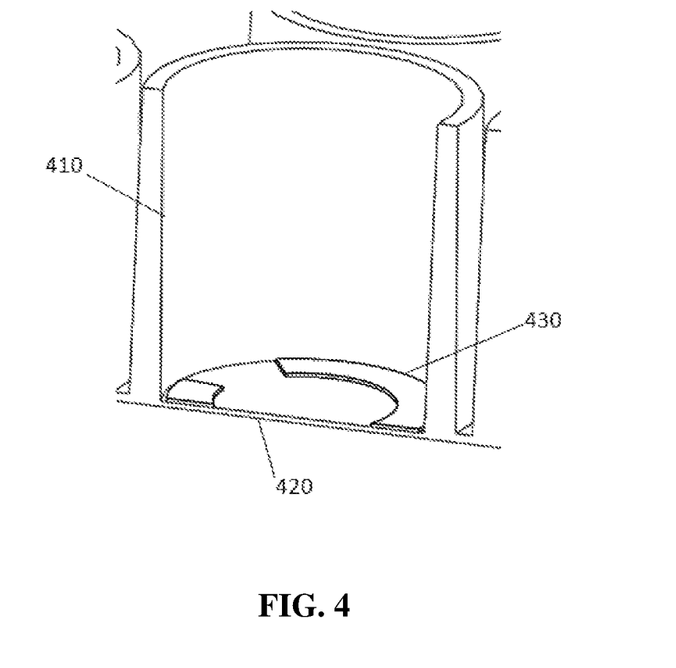
FIG. 4 depicts a cross section of a well that includes a partial ring spacer.
Figure 5:
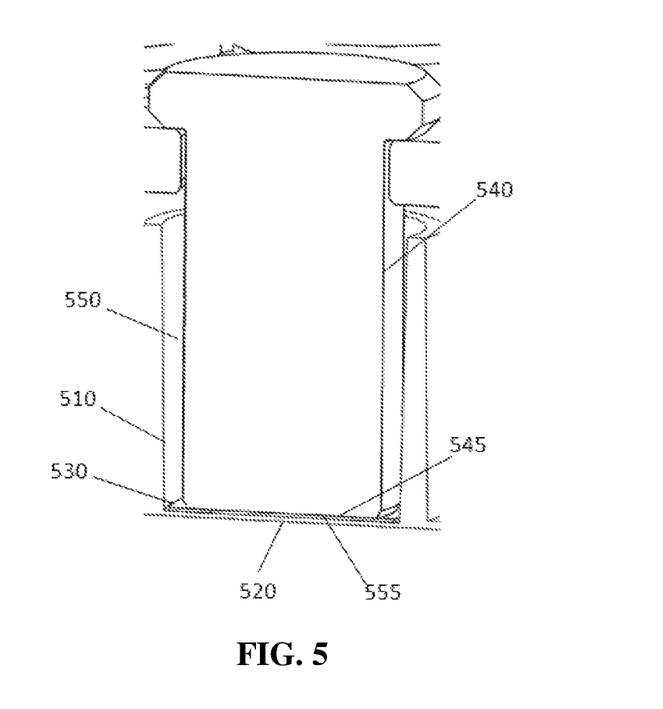
FIG. 5 depicts a cross section of a well with a partial ring spacer and an inserted pillar.

FIGS. 3 to 5 show an embodiment in which the spacer is a partial (e.g. having a gap) flattened ring. Although these figures depict examples in which the ring has a gap, it should be appreciated that some embodiments can utilize a flattened ring spacer that forms a complete circle (i.e. lacks a gap). FIG. 3 shows an example of such a ring 330, with a gap 360. FIG. 4 depicts a well of a microwell plate having a wall 410 and a floor 420, with a partial flattened ring spacer 430 placed on the floor of the well. FIG. 5 shows an example of a well of a multiwell plate that utilizes a partial flattened ring as a spacer, into which a pillar has been inserted. As shown, the well has a side 510 and a floor 520 on which rests a partial flattened ring 530. A pillar 540 is inserted into the well, and has a lower face 545 that rests on top of the partial flattened ring. The pillar is sized and positioned within the well to provide a lateral gap 550 between the side of the well and the lateral wall of the pillar. A controlled height gap 555 is generated between the lower face of the pillar and the floor of the well by virtue of the pillar resting on the partial flattened ring spacer. Addition of a polymerizable or gel-forming liquid to a well so arranged (or the presence of such a polymerizable or gel-forming liquid prior to or at insertion of the pillar into the well) can result in the formation of a controlled thickness gel layer within the controlled height gap, which remains in place upon removal of the pillar from the well. Although depicted in FIGS. 4 and 5 as being placed on the floor of a well, in some embodiments a partial flattened ring spacer can be placed on the lower face of a pillar.

Although depicted as a circular ring, a partial flattened ring spacer can be of any suitable shape, including oval, square, rectangular, pentagonal, hexagonal, polygonal, or irregular. Similarly, a partial flattened ring spacer can be of any suitable composition capable of providing sufficient mechanical support for a pillar. Suitable materials include synthetic polymers (e.g. polyethylene, polypropylene, polystyrene, polyamide, silicon, etc.), biopolymers (e.g. crosslinked gelatin, crosslinked polysaccharides, etc.), metals (e.g. stainless steel, titanium, etc.), and/or minerals. A ring spacer can be encoded (e.g. by color and/or barcode) to indicate the type of ring spacer selected and provide information regarding the contents and/or gel depth in a particular well. In some embodiments a ring spacer can include growth factors and/or other components that can influence cell growth proximate to the spacer.

Figure 6:
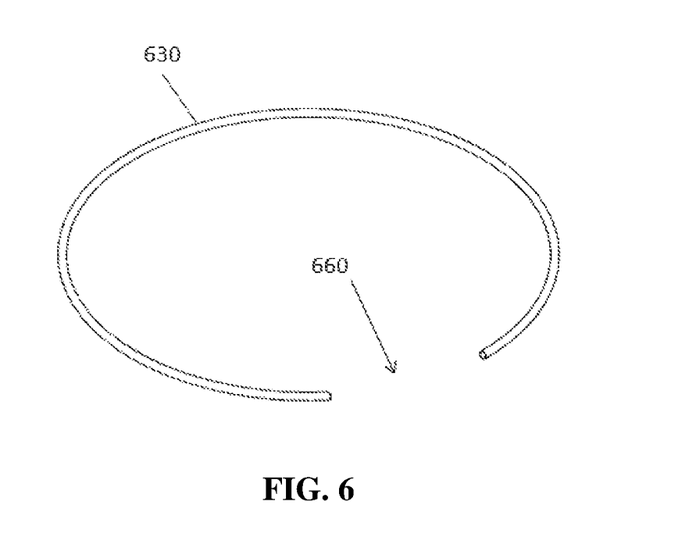
FIG. 6 depicts a partial toroidal spacer of the inventive concept.
Figure 7:
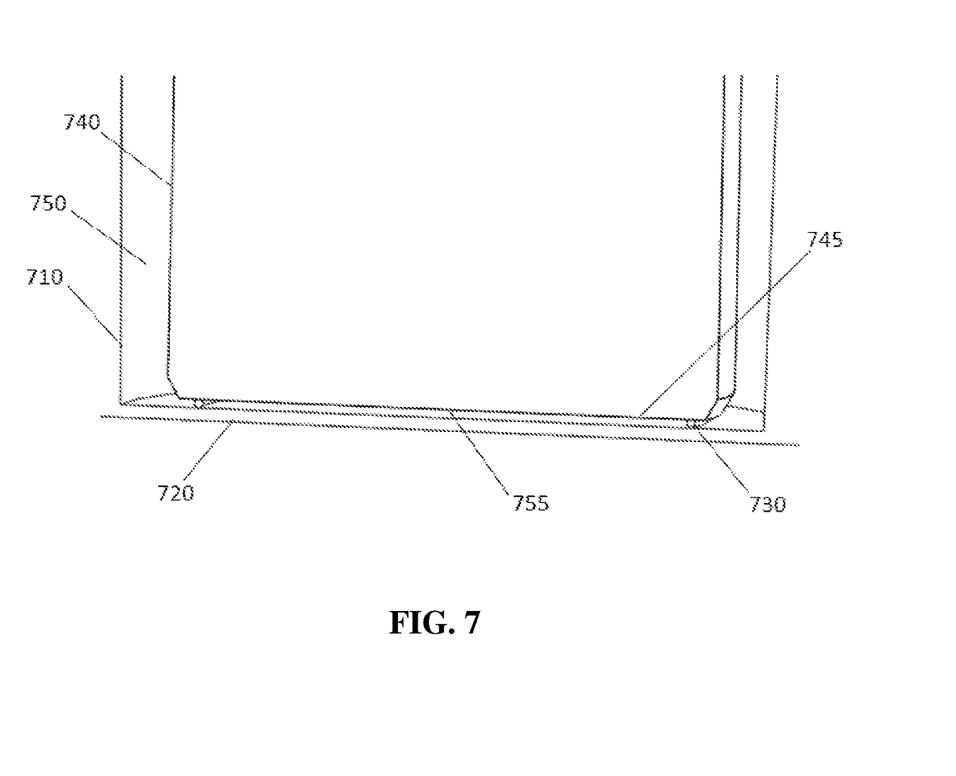
FIG. 7 depicts a cross section of a well with a partial toroidal spacer and an inserted pillar.

FIGS. 6 and 7 show embodiments of a partial (e.g. having a gap) toroidal spacer of the inventive concept. Although these figures depict examples in which the toroidal spacer has a gap, it should be appreciated that some embodiments can utilize a toroidal spacer that forms a complete circle (i.e. lacks a gap). FIG. 6 shows an example of a partial toroidal spacer 630, with a gap 660. FIG. 7 shows an example of a well of a multiwell plate that utilizes a partial toroid as a spacer, into which a pillar has been inserted. As shown, the well has a side 710 and a floor 720 on which rests a partial toroidal spacer 730. A pillar 740 is inserted into the well, and has a lower face 745 that rests on top of the partial toroidal spacer. The pillar is sized and positioned within the well to provide a lateral gap 750 between the side of the well and the lateral wall of the pillar. A controlled height gap 755 is generated between the lower face of the pillar and the floor of the well by virtue of the pillar resting on the partial toroidal spacer. Addition of a polymerizable or gel-forming liquid to a well so arranged (or the presence of such a polymerizable or gel-forming liquid prior to or at insertion of the pillar into the well) can result in the formation of a controlled thickness gel layer within the controlled height gap, which remains in place upon removal of the pillar from the well. Although depicted in FIGS. 6 and 6 as being placed on the floor of a well, in some embodiments a partial toroidal spacer can be placed on the lower face of a pillar.

A partial toroidal spacer can be constructed using a loop of flexible or pliant material having a circular cross section. Suitable materials include wires, cords, strings, and extruded fibers. Similarly, a partial toroidal spacer can be of any suitable composition capable of providing sufficient mechanical support for a pillar. Suitable materials include synthetic polymers (e.g. polyethylene, polypropylene, polystyrene, polyamide, silicon, etc.), biopolymers (e.g. crosslinked gelatin, crosslinked polysaccharides, etc.), metals (e.g. stainless steel, titanium, etc.), and/or minerals. A toroidal spacer can be encoded (e.g. by color and/or barcode) to indicate the type of toroidal spacer selected and provide information regarding the contents and/or gel depth in a particular well. In some embodiments a toroidal spacer can include growth factors and/or other components that can influence cell growth proximate to the spacer.

In some embodiments the spacer(s) is/are affixed to the floor of the well. In other embodiments the spacer(s) is/are affixed to the flat lower face of the pillar. In still other embodiments a portion of the spacers are affixed to the floor of the well and another portion are affixed to the flat lower face of the pillar. Alternatively, one or more spacers can be free objects that are not affixed to either of the well or the pillar. Such free spacers can, for example, be placed in a well or wells of a plate prior to insertion of a pillar into the well. Such a spacer can be added prior, during, or following addition of the gel-forming solution to the well. Spacers can be dimensioned to provide a distance of from 10 μm to 5 mm between the floor of the well and the flat lower face of the pillar on insertion into the well. It should be appreciated that the use of such spacers and removable or slidable "floating" pillars provides a solution to the problem of uneven well depth and/or height in cast multiwell plates by providing a gel bed on consistent depth.

Wells, spacers, and pillars can be constructed of any suitable material, preferably a biocompatible material. In some embodiments a wall and/or floor of a well can include a porous material, such as a porous membrane. In order to facilitate observation of the cultured cells at least a portion of the well or the floor of the well can be constructed of a material that is at least partially transparent (e.g. greater than 10% transmissive) of a visible and/or ultraviolet wavelength. It should be appreciated that such transparency can facilitate the use of gel formulations in which gel formation is activated by exposure to ultraviolet or visible light. Suitable materials include polystyrene, glass, polycarbonate, and polyacrylate, to name a few. Spacers can be constructed of any compatible material that provides sufficient mechanical strength to support the pillar. Suitable materials include polymers (e.g. polycarbonate, silicone, etc.), ceramics, glasses, and metals.

Pillars can similarly be constructed of any suitably compatible material that can provide sufficient rigidity for insertion into the well and to support a mechanically stable flat lower face. In a preferred embodiment the pillar is at least partially constructed of a hydrophobic and/or "non-stick/low friction polymer or coating, such as stainless steel or a fluoropolymer, in order to facilitate removal from the well following gel formation. In some embodiments a pillar can be at least partially constructed of a magnetically responsive material in order to facilitate manipulation using a magnetic field.

Another embodiment of the inventive concept is a method for providing a gel bed of consistent thickness and having a flat upper surface in one or more wells. In such a method one or more well having a side wall and a floor are instilled with a gel-forming solution. In some embodiments the well can include a spacer (as described above) prior to addition of the gel-forming solution. In such embodiments the spacer (or one or more of multiple spacers) can be attached to the floor of the well. Following addition of the gel-forming solution and prior to formation of the gel a pillar is inserted into the volume defined by the well and lowered until the flat lower face of the pillar and the floor of the well are both in contact with the spacer(s). In some embodiments the spacer (or one or more of multiple spacers) is coupled to the lower surface of the pillar. Gel formation can be initiated following insertion of the pillar (for example, by exposure to appropriate wavelengths or changes in temperature) or, alternatively, prior to insertion of the pillar (provided that gel formation is not complete prior to insertion of the pillar). After sufficient time has passed for gel formation to have progressed to the point of forming a mechanically stable gel the pillar can be removed. In some embodiments gel formation can continue following removal of the pillar from the well.

In some multiple well embodiments multiple pillars can be provided in a rack or similar device that orients the pillars and distributes them to reflect the distribution of the multiple wells. In such embodiments the pillars can be engaged in the rack in a manner that allows them to slide along their major axis, permitting insertion into and removal from wells without moving the rack. In such embodiments the pillars can include a magnetically responsive material that permits manipulation of the pillars by a magnetic field. Alternatively, a vacuum can be applied to lift the floating pillars by pressure differential. In other embodiments the pillars can be coupled to one another such that they can be moved in unison.

Figure 8A:
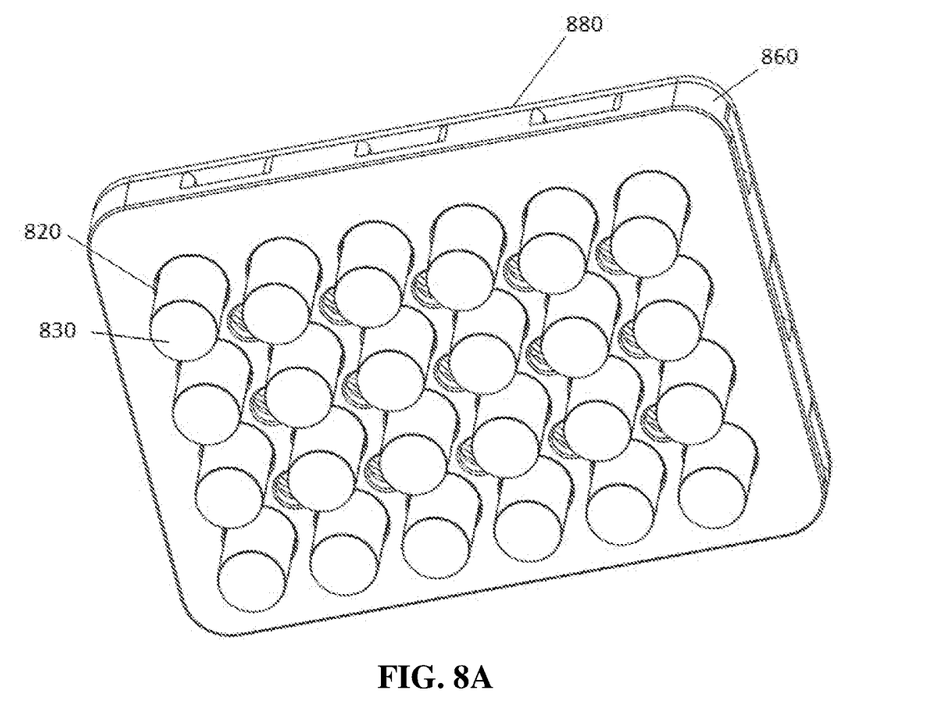
FIG. 8A depicts an orthogonal view of an assembly with an array of floating, translatable pillars mounted in a manifold.
Figure 8B:
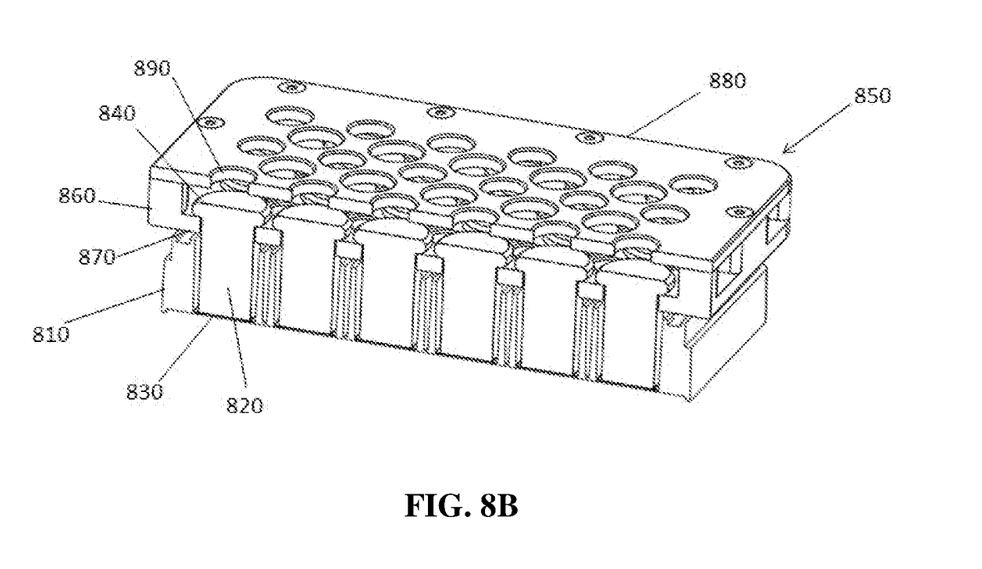
FIG. 8B depicts a cross section of the assembly of FIG. 8A inserted into an array of wells in a microplate.

An example of an assembly of the inventive concept is shown in FIGS. 8A and 8B. FIG. 8A depicts an orthogonal view of such an assembly. FIG. 8B provides a cross section of such an assembly in which the pillars are inserted in the wells of a microplate. As shown, the microwell plate 810 has multiple wells into each of which a pillar 820 is inserted.

Each pillar has a lower face 830 and an upper portion 840. The assembly also includes a manifold 850 that includes a body 860 and a cover 880. A spacing device (not shown) can be interposed between such a microwell plate and the manifold, to aid in or adjust the positioning of the pillars within the wells of the plate. Such a spacer can be an open quadrilateral dimensioned to contact the periphery of the microwell plate when in position and having a large central opening that provides access for the pillars to the wells of the plate. The body includes body apertures 870 associated with the pillars. The body apertures are dimensioned to allow translational movement of a portion of the associated pillar through the body aperture along the pillar's major axis; the head of the pillar is dimensioned to prevent movement of the head portion of the through the associated body aperture and stop movement of the pillar as it contacts the cover of the manifold. This arrangement allows each pillar to slide through the associated body aperture while permitting it to be retained with the manifold (e.g. on removal from the microwell plate). In such an arrangement the pillars are considered to be slidably associated, i.e. translational movement of a pillar is allowed while retaining at least a portion of the pillar within the manifold. It should be appreciated that such an arrangement allows for the formation of gel or polymer layers within the wells of the microwell plate that have extremely consistent thickness (both within a well and between wells) as the movement of the pillars reduces the effects of variations within or between the wells (e.g. floor height and/or thickness) and/or pillars. This consistency both improves reproducibility and simplifies analysis, in particular imaging operations within the wells.

A variety of forces can be applied to provide such a sliding motion. For example, if the pillars are constructed at least in part using a magnetically responsive material a magnetic field can be applied to the manifold on the side opposing the microwell plate into which the pillars are inserted. Alternatively, a vacuum can be applied to the manifold to induce a pressure differential that applied force to the pillars. This can be facilitated by the inclusion of one or more cover apertures 890. In still other embodiments the manifold can be physically removed from the microwell plate (for example, manually or through the use of a robotic device that grips or interfaces with the manifold), the sliding of the pillars reducing mechanical stress of gels or polymerized materials deposited in the wells of the microwell plate during this process.

It should be appreciated that although FIG. 8 depicts an embodiment in which each of the pillars can slide independently, in some embodiments two or more pillars can be joined (for example, at their upper portions) to provide a subset of pillars that move in concert. Such an arrangement allows the joined pillars to move in concert, and can be used to provide a system in which removal time of such a group of pillars (for example, the permit a washing step that halts polymerization at a desired stage) is carefully controlled.

Figure 9:
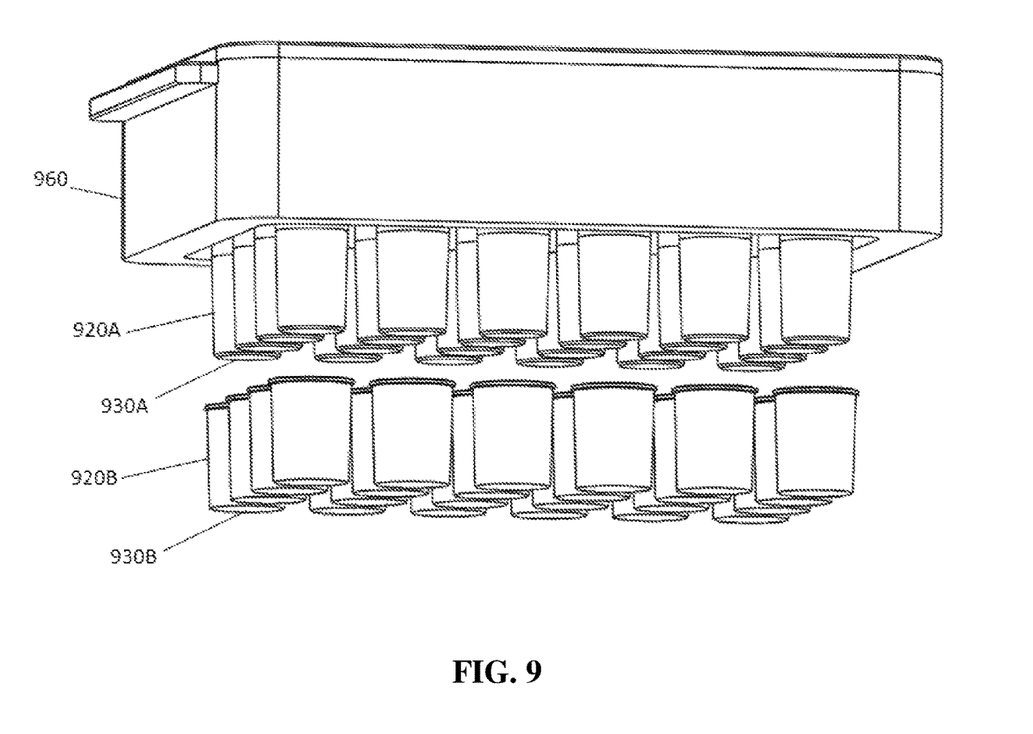
FIG. 9 depicts an assembly of pillars in a manifold configured for use with disposable sleeves that fit over each pillar.

As noted above, such an assembly of pillars can be configured as a single use device or a multiple use device. In some embodiments a manifold/pillars assembly can be used in conjunction with removable sleeves that cover the lower face and at least a portion of the body of the pillars. An example of such an embodiment is shown in FIG. 9. FIG. 9 depicts an assembly that includes a manifold 960 that supports a number of pillars 920A arranged in an array with an exposed lower face 930A. Removable sleeves are provided with a wall 920B dimensioned to fit over the pillars and a sleeve lower face 930B, both of which contact gel or polymer precursor solutions when placed over the pillars and in use. In some embodiments the lower face of the pillar can include features (for example, an inset) that interface with the sleeve and assist in temporarily securing it over the pillar. Such an arrangement advantageously permits re-use of the pillar and manifold assembly while utilizing disposable single-use sleeves to reduce potential contamination (e.g. via carryover) of gel or polymer precursor solutions. In some embodiments the manifold can include features (such as movable panels) that facilitate removal of sleeves from the pillars after use. Such sleeves can be made of any suitable material, including hydrophobic and/or low friction polymers, and can be provided in an array sized and positioned to correspond to pillars of a manifold/pillar assembly.

Figure 10:
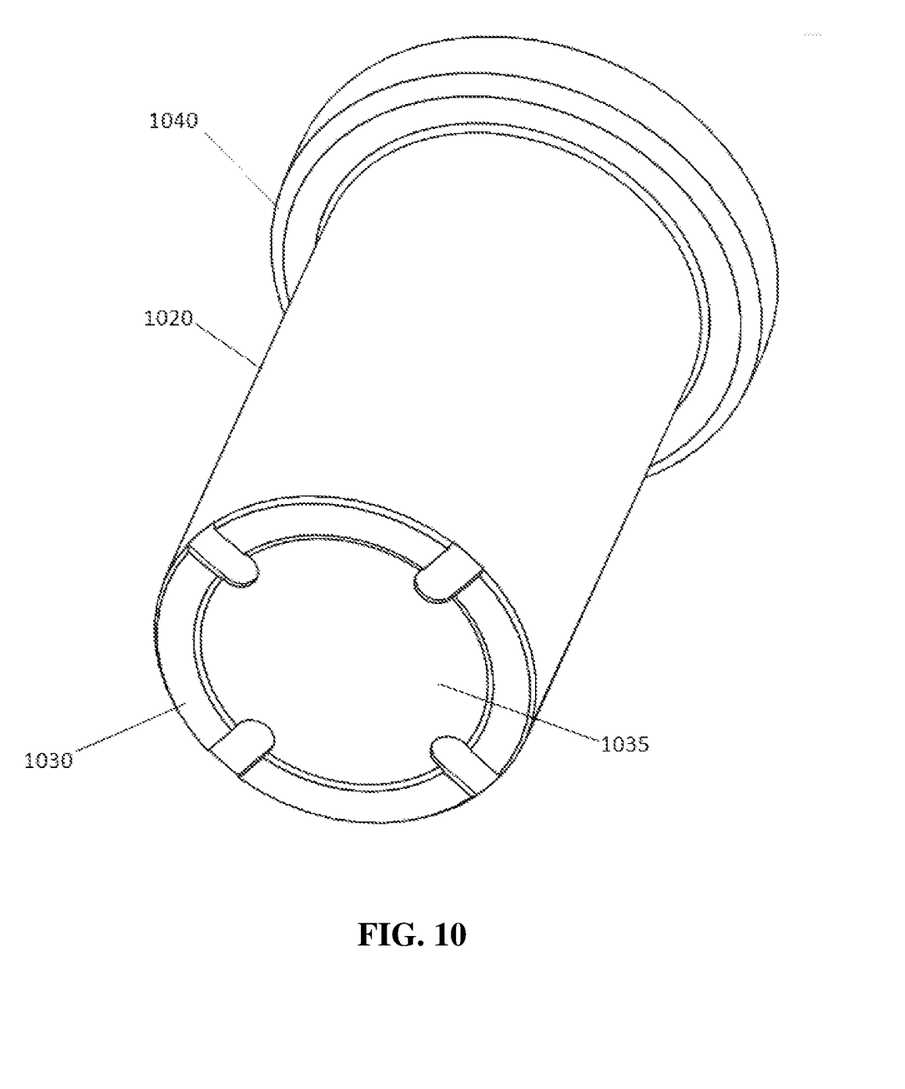
FIG. 10 depicts a pillar in which the lower face includes an indentation.

Although generally described above as having planar or essentially planar lower faces, in some embodiments one or more pillars can have lower faces that incorporate features for patterning or shaping the gel or polymer cast on the test surface in a desired pattern or configuration. For example, in such embodiments the lower face of a pillar (or a sleeve covering a pillar) can include one or more depressions and/or protrusions. These can be arranged or positioned in a regular or geometric arrangement, or can be randomly arranged or positions. In some embodiments such a lower face can include features that imprint a shape corresponding to an organ or tissue model on the polymer layer. Such patterning features can, for example, be selected to encourage (or, alternately, discourage) attachment and/or proliferation of specific cells or cell types to specific regions of the resulting patterned polymer surface. Similarly, such patterning or shaping can, for example, be utilized to provide different regions within the deposited gel or polymer that are utilized for culture or study of different cell types, or to provide surface textures or features that aid in cell adhesion or release. An example of such a pillar is shown in FIG. 10. FIG. 10 depicts a pillar 1020 with an expanded top portion 1040 that provides retention in a manifold that permits lateral movement along the primary axis of the pillar. The pillar also includes a lower face 1030 that includes a patterning or shaping feature, in this instance an inset 1035. Such an inset provides a slightly raised central portion in the final gel or polymer layer following casting.

Another embodiment of the inventive concept is a method for generating a controlled thickness gel or polymer layer on a test surface (for example, on the floor of a well of a microplate). In such methods a spacing device is interposed between a test surface and the lower face of a pillar that is able to move translationally along its major axis, such that the lower face of the pillar is in free contact (i.e. contact without being coupled) with the spacing device. This action defines a volume between the test surface and the lower face of the pillar. A gel or polymer precursor is provided as a solution or suspension that occupies this space. Such a gel or polymer precursor can be present at the test surface at the time of pillar insertion, instilled into or onto the test surface at the time of pillar insertion (e.g. via a space between a wall surrounding the test surface and the side of the pillar), or instilled into or onto the test surface after the pillar has been inserted. Suitable gel precursors include hydrophilic biomolecule polymers, such as gelatin, agarose, alginate, etc., at temperatures or buffer compositions that permit the gel precursor to flow as a fluid. Suitable polymer precursors can include water soluble monomers (such as acrylamide monomers), crosslinkers, and/or activatable initiators. Once the gel or polymer precursor is present in the defined space between the test surface and the lower face of the pillar gel or polymer formation can be initiated. For example, temperature can be lowered and/or suitable divalent cations provided to initiate gel formation of a gel precursor solution. Similarly, visible or ultraviolet irradiation can be used to initiate polymer formation in a polymer precursor solution.

After the gel or polymer layer has formed the pillar can be removed. The mechanism for pillar removal depends upon the method by which the pillar or pillars have been applied. When arrayed pillars mounted in a manifold are used, pillars can be extracted by, for example, application of low pressure or vacuum to the manifold, exposure of pillars incorporating magnetically responsive material to a magnetic field, and/or lifting of the manifold away from the test surface.

Following removal of the pillars the exposed gel or polymer surface can be subjected to further treatment. For example, the gel or polymer layer can be washed and contacted with a cell culture media. Alternatively, compounds that facilitate cell localization (e.g. receptors) or cell behavior (e.g. growth factors) can be applied to the gel or polymer layer.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A device for generating a patterned hydrogel, comprising:
    a well comprising a lateral wall and a floor, the lateral wall and the floor defining an internal volume;
    a floating pillar dimensioned to lie within the internal volume and comprising a lower face, wherein the floating pillar is translatably coupled to a pillar support and positioned to correspond to the well; and
    a spacer interposed between the lower face of the floating pillar and the floor of the well, and configured to provide a separation distance between the floor and the lower face in the device, wherein the spacer is selected from the group consisting of one or more beads, a torus, a partial torus, and one or more polygons.

2. The device of claim 1, wherein the spacer is coupled to the floor.

3. The device of claim 1, wherein the spacer is coupled to the lower face.

4. The device of claim 1, wherein at least one linear dimension of the spacer corresponds to the separation distance.

5. The device of claim 1, wherein at least a portion of the floor comprises a material transmissive of one or more wavelengths selected from the group consisting of an optical wavelength and an ultraviolet wavelength.

6. The device of claim 1, further comprising a plate portion that comprises a plurality of wells.

7. The device of claim 6, comprising a plurality of floating pillars, wherein the plurality of floating pillars are translatably coupled to a pillar support and positioned to correspond to at least a portion of the plurality of wells.

8. The device of claim 1, comprising a removable sleeve dimensioned to fit over the floating pillar and comprising a sleeve lower face.

9. The device of claim 1, wherein the lower face is essentially planar.

10. The device of claim 1, where the lower face comprises a patterned surface.

* * * * *